United States Patent
Santobianco et al.

(10) Patent No.: US 6,797,841 B2
(45) Date of Patent: Sep. 28, 2004

(54) AMINOBENZOPHENONES AND PHOTOPOLYMERIZABLE COMPOSITIONS INCLUDING THE SAME

(75) Inventors: John Gabriel Santobianco, Ocean Springs, MS (US); Rajamani Nagarajan, Ocean Springs, MS (US); August John Muller, Mobile, AL (US); Joseph Stanton Bowers, Jr., Mobile, AL (US)

(73) Assignee: Albemarle Corporation, Baton Rouge, LA (US)

( * ) Notice: Subject to any disclaimer, the term of this patent is extended or adjusted under 35 U.S.C. 154(b) by 0 days.

(21) Appl. No.: 10/261,733

(22) Filed: Oct. 1, 2002

(65) Prior Publication Data

US 2003/0078313 A1 Apr. 24, 2003

Related U.S. Application Data

(63) Continuation of application No. 09/368,034, filed on Aug. 3, 1999, now Pat. No. 6,479,706, which is a continuation-in-part of application No. 09/017,852, filed on Feb. 3, 1998, now abandoned.
(60) Provisional application No. 60/037,155, filed on Feb. 4, 1997.

(51) Int. Cl.$^7$ ............... C07C 211/00; C07C 221/00; C07D 209/56; C08F 2/46
(52) U.S. Cl. ............ 564/323; 564/328; 548/435; 548/451; 522/8; 522/13
(58) Field of Search .............. 564/323, 328; 548/435, 451; 522/8, 13; 568/332

(56) References Cited

U.S. PATENT DOCUMENTS

| | | |
|---|---|---|
| 3,366,691 A | 1/1968 | Keller |
| 3,595,900 A | 7/1971 | Loudas et al. |
| 3,833,658 A | 9/1974 | Avar et al. |
| 3,989,609 A | 11/1976 | Brack |
| 4,007,209 A | 2/1977 | Hickmann et al. |
| 4,043,887 A | 8/1977 | Pacifici et al. |
| 4,080,382 A | 3/1978 | Pacifici et al. |
| 4,113,593 A | 9/1978 | Barzynski et al. |
| 4,199,420 A | 4/1980 | Photis |
| 4,218,294 A | 8/1980 | Brack |
| 4,234,712 A | 11/1980 | Keller et al. |
| 4,374,984 A | 2/1983 | Eichler et al. |
| 4,390,565 A | 6/1983 | Fonda |
| 4,507,497 A | 3/1985 | Reilly, Jr. |
| 4,518,788 A | 5/1985 | Crivello |
| 4,528,081 A | 7/1985 | Lien et al. |
| 4,529,490 A | 7/1985 | Crivello et al. |
| 4,576,975 A | 3/1986 | Reilly, Jr. |
| 4,577,034 A | 3/1986 | Durvasula |
| 4,584,260 A | 4/1986 | Iwasaki et al. |
| 4,602,097 A | 7/1986 | Curtis |
| 4,661,434 A | 4/1987 | Iwasaki et al. |
| 4,666,951 A | 5/1987 | Onishi et al. |
| 4,691,059 A | 9/1987 | Mitra et al. |
| 4,701,478 A | 10/1987 | Jellinek et al. |
| 4,714,726 A | 12/1987 | Ketley |
| 4,727,868 A | 3/1988 | Szycher et al. |
| 4,755,450 A | 7/1988 | Sanders et al. |
| 4,767,797 A | 8/1988 | Ai et al. |
| 4,843,179 A | 6/1989 | Jansons et al. |
| 4,935,330 A | 6/1990 | Hofmann et al. |
| 4,940,645 A | 7/1990 | Davis et al. |
| 4,975,471 A | 12/1990 | Hayase et al. |
| 4,990,589 A | 2/1991 | Towle et al. |
| 5,145,885 A | 9/1992 | Berner et al. |
| 5,229,238 A | 7/1993 | Kobayashi et al. |

(List continued on next page.)

FOREIGN PATENT DOCUMENTS

| | | |
|---|---|---|
| DE | 18 07 740 | 9/1970 |
| DE | 27 29 918 | 1/1979 |
| DE | 36 06 155 A | 8/1987 |
| DE | 43 03 938 A | 8/1993 |
| EP | 0 150 891 A | 8/1985 |
| FR | 2 138 875 A | 1/1973 |
| FR | 2617160 | 12/1988 |
| GB | 1412731 | 11/1975 |
| GB | 2 075 506 A | 11/1981 |
| JP | 8-12630 | 1/1996 |
| WO | WO 96/33156 | 10/1996 |

OTHER PUBLICATIONS

Hellerman et al., "Syntheses of Certain Derivatives of Phenylalanine and of Auramine in Studies of Antimalarial Action," *J. Amer. Chem. Soc.*, vol. 68(10), pp. 1890–1893, Oct. 17, 1946.
Pindur et al., "[4+2]Cycloaddition of indole derivatives with bismaleimides: a route to new biscarbazoles," *J. Chem. Soc., Perkin Trans. 1*, No. 12, pp. 1861–1867, Jun. 21, 1997.
Patent Abstracts of Japan, vol. 011, No. 282 (C–446), Sep. 11, 1987 & JP 62 081403 A, Apr. 14, 1987.
Patent Abstracts of Japan, vol. 012, No. 143 (C–492), Apr. 30, 1988 & JP 62 257969, Nov. 10, 1987.
Database WPI, Section Ch, Week 8501, Derwent Publications, London, GB; AN 85–004014 XP002066202 & JP 59 204 850 A.
Database WPI, Section Ch, Week 9435, Derwent Publications, London, GB; AN 94–283314 XP002066200 & JP 06 211 759 A.
Database WPI, Section Ch, Week 9435, Derwent Publications, London, GB; AN 94–283313 XP002066201 & JP 06 211 758 A.
Database WPI, Section Ch, Week 9607, Derwent Publications, London, GB; AN 96–066076 XP002066203 & JP 07 325 391 A.

*Primary Examiner*—Johann Richter
*Assistant Examiner*—Sikarl A. Witherspoon
(74) *Attorney, Agent, or Firm*—Alston & Bird LLP

(57) ABSTRACT

Novel benzophenone derivatives and methods of making and using the same are disclosed. The novel compounds can display highly active photoinitiation and photopolymerization properties.

36 Claims, 2 Drawing Sheets

U.S. PATENT DOCUMENTS

| | | |
|---|---|---|
| 5,310,862 A | 5/1994 | Nomura et al. |
| 5,378,519 A | 1/1995 | Kikuchi et al. |
| 5,393,627 A | 2/1995 | Nakamura et al. |
| 5,428,163 A | 6/1995 | Mills |
| 5,436,279 A | 7/1995 | Grundke et al. |
| 5,468,904 A | 11/1995 | Osawa et al. |
| 5,504,391 A | 4/1996 | Turner et al. |
| 5,573,889 A | 11/1996 | Hofmann et al. |
| 5,629,356 A | 5/1997 | Desobry et al. |
| 5,686,503 A | 11/1997 | Nohr et al. |

AMINOBENZOPHENONES AND PHOTOPOLYMERIZABLE COMPOSITIONS INCLUDING THE SAME

CROSS-REFERENCE TO RELATED APPLICATION

This application is a continuation application of application Ser. No. 09/368,034, filed Aug. 3, 1999, now U.S. Pat. No. 6,479,706 which is a continuation-in-part application of application Ser. No. 09/017,852, filed Feb. 3, 1998, now abandoned, which is related to commonly owned Provisional Application Ser. No. 60/037,155, filed Feb. 4, 1997. This application is also related to pending application Ser. No. 08/858,268, filed May 19, 1997, which is related to commonly owned Provisional Application Ser. No. 60/017,127, filed May 20, 1996. All of the above-described applications are incorporated in their entirety by reference.

FIELD OF THE INVENTION

This invention relates generally to novel photoactive compounds and methods for using the same. More particularly, this invention relates to aminobenzophenones and methods of using the same in photoactivatable polymerization systems.

BACKGROUND OF THE INVENTION

Ethylenically unsaturated compounds, and in particular acrylate derivatives, can be polymerized by irradiation with ultraviolet light of wavelength between 200 and 450 nanometers (nm) in the presence of a bimolecular photoinitiating system. The photoinitiating system can include, for example, (1) a benzophenone derivative and (2) a coinitiator or synergist, that is, a molecule which serves as a hydrogen atom donor. The coinitiators or synergists are typically alcohols, tertiary amines or ethers which have available hydrogens attached to a carbon adjacent to a heteroatom.

One commercially available benzophenone derivative useful as a photoinitiator is 4,4'-bis(dimethylamino) benzophenone, also referred to in the art as "Michler's Ketone". Michler's Ketone has the following structure:

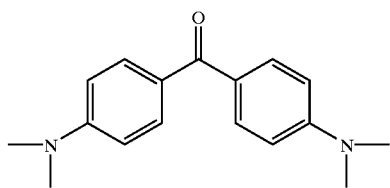

While Michler's Ketone can be useful as a photoinitiator in radiation curing of polymers, it is typically used little in the industry due to its potentially hazardous characteristics.

4,4'-Bis(diethylamino)benzophenone (also referred to as tetraethyl Michler's Ketone) has been proposed as a possible alternative to Michler's Ketone due to its lower toxicity. However, this compound does not exhibit good photoinitiating activity and thus has not been widely adopted as an alternative to Michler's Ketone.

Other Michler's Ketone derivatives are described, for example, in U.S. Pat. No. 4,507,497 to Reilly, Jr., which is directed to water soluble Michler's Ketone analogs which include amino groups substituted by $R^1COOH$, in which $R^1$ is an alkylene group having 1 to 8 carbon atoms.

Examples of other commercially available photoinitiators useful in bimolecular photoinitiator systems include benzophenone, 2,4-dimethylbenzophenone, isopropylthioxanthone, and 2,4-diethylthioxanthone. The UV absorption spectrum for these individual photoinitiators, however, do not match-up efficiently with the UV emission spectra of the standard commercially available mercury vapor bulbs.

Thus, commercially viable UV curing processes can require a relatively large amount of initiator and synergist incorporated into the formulation. This can lead to cured articles which contain high levels of residual photoinitiator and synergist, which in turn can result in decreased light fastness and lower resistance to oxidative degradation. In addition, the residual photoinitiator and synergist can be extracted or leach out of the cured article or migrate to the surface of the article. Many times the physical properties of the article are degraded by the presence of the residual photoinitiator and synergist.

SUMMARY OF THE INVENTION

It is accordingly an object of the present invention to provide compounds which can be used as photoinitiators in photopolymerization processes. It is also an object of the invention to provide compounds which exhibit useful photoinitiation activity with minimal or no adverse hazardous characteristics. These and other objects of the present invention will become apparent from the following general and detailed description of the invention.

The objects of the present invention are achieved based on the discovery of novel compounds useful in photopolymerization systems. The compounds can display highly active photoinitiation and photopolymerization properties with minimal or no adverse hazardous characteristics. Specifically the compounds can be essentially or substantially non-mutagenic. As is well known in the art, photoinitiator that is not consumed in the photopolymerization reaction may be extracted or leached from the cured product. Therefore a non-mutagenic photoinitiator is especially desirable.

Still further, the compounds can have desirable ultraviolet wavelength absorbance, which in turn can provide advantages when using narrow wavelength lamps. In this regard, advantageously the compounds possess UV spectra with significant absorption bands between 250 and 350 nm and in particular between 290 and 325 nm. Accordingly, the compounds can be irradiated with a narrow wavelength band, high pressure fill UV curing lamp known as an excimer lamp with spectral emphasis in the 250 to 350 nm range, and in particular with its peak emission wavelength at or near 308 nm, as described in U.S. Pat. No. 5,504,391.

Compounds showing a significantly elevated level of reactivity at these wavelengths can be used in considerably lower amounts. For example, when the compounds of the invention are used with an excimer lamp versus a medium pressure mercury lamp, only about one-fourth of the amount of photoinitiator can be required to give equivalent cure speeds. In addition, when the same concentration of photoinitiator is used with both an excimer and a medium pressure mercury lamp the excimer lamp can provide greatly increased cure speeds. Because less photoinitiator is required, less residual photoinitiator can remain in the cured articles, thereby minimizing problems associated with leaching or extraction, decreased light fastness and lower resistance to oxidative degradation.

The compounds of the invention have a structure according to Formula (I) below:

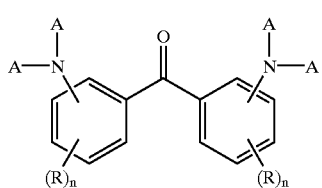

wherein:
each A is independently selected from the group consisting of hydrogen, lower alkyl, cycloalkyl, aryl, lower alkanol, lower alkoxy, halogen, sulfonyl, alkylsulfonyl, trihaloalkyl, trihaloalkoxy, trihaloalkylthio, polymerizable moiety, and oligomeric moiety, with the proviso that no more than three A are the same lower alkyl;
each R is independently selected from the group consisting of hydrogen, lower alkyl, cycloalkyl, aryl, lower alkanol, lower alkoxy, halogen, sulfonyl, alkylsulfonyl, trihaloalkyl, trihaloalkoxy, trihaloalkylthio, polymerizable moiety, and oligomeric moiety; and
n is an integer from 1 to 4.

The present invention also provides photopolymerizable compositions which include the compounds of Formula (I) above as a component thereof, as well as methods for the manufacture of the compounds of Formula (I) and methods for the use of the compounds of Formula (I) in photopolymerization systems.

BRIEF DESCRIPTION OF THE DRAWINGS

Some of the features and advantages of the invention having been described, others will become apparent from the detailed description which follows, and from the accompanying drawings, in which.

DETAILED DESCRIPTION OF THE INVENTION

Figure 1:
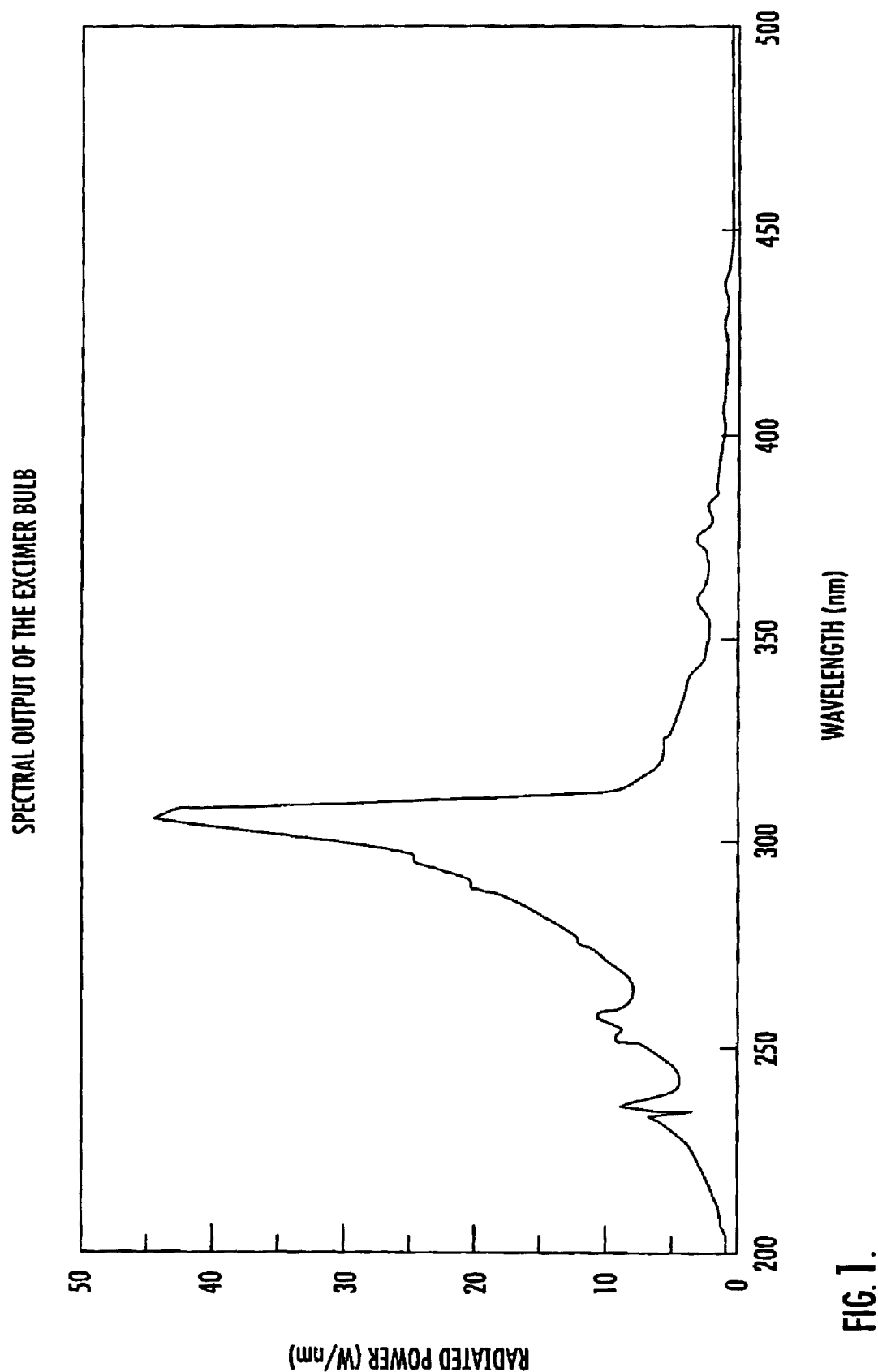
FIG. 1 illustrates the ultraviolet (UV) emission spectrum of an excimer lamp as described in U.S. Pat. No. 5,504,391.

The novel compounds of the invention include compounds according to Formula (I) below:

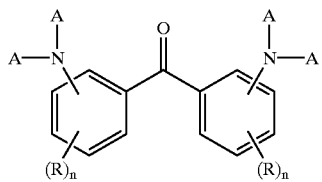

wherein:
each A is independently selected from the group consisting of hydrogen, lower alkyl, cycloalkyl, aryl, lower alkanol, lower alkoxy, halogen, sulfonyl, alkylsulfonyl, trihaloalkyl, trihaloalkoxy, trihaloalkylthio, polymerizable moiety, and oligomeric moiety, with the proviso that no more than three A are the same lower alkyl;
each R is independently selected from the group consisting of hydrogen, lower alkyl, cycloalkyl, aryl, lower alkanol, lower alkoxy, halogen, sulfonyl, alkylsulfonyl, trihaloalkyl, trihaloalkoxy, trihaloalkylthio, polymerizable moiety, and oligomeric moiety; and
n is an integer from 1 to 4.

As used herein, the term lower alkyl refers to linear or branched C1-C8 alkyl, such as but not limited to methyl, ethyl, propyl, isopropyl, n-butyl, t-butyl, and the like, optionally substituted with one or more halogen, aryl, arylalkyl, alkylaryl, cycloalkyl, alkoxy, heteroatom, and the like. The term cycloalkyl refers to C3 to C6 cyclic alkyl, such as but not limited to cyclopropyl, cyclobutyl, cyclopentyl and cyclohexyl, optionally substituted with one or more halogen, aryl, alkyl, arylalkyl, alkylaryl, cycloalkyl, alkoxy, heteroatom, and the like. The term alkanol refers to lower alkyl substituted with one or more hydroxyl groups. The term lower alkoxy refers to lower alkyl substituted with one or more oxygen atoms, including but not limited to methoxy, ethoxy, propoxy, butoxy, and the like. The term alkylsulfonyl refers to lower alkyl substituted with sulfonyl. The terms trihaloalkyl, trihaloalkoxy, and trihaloalkylthio refer to lower alkyl, lower alkoxy and lower alkylthio, respectively, in which hydrogen atoms on the organic group are replaced with halogen, preferably fluorine. The term aryl refers to C3 to C10 cyclic aromatic groups such as but not limited to phenyl, naphthyl, and the like, optionally substituted with one or more halogen, alkyl, arylalkyl, alkylaryl, cycloalkyl, alkoxy, heteroatom, and the like. The term heteroatom refers to oxygen, nitrogen, sulfur or phosphorous.

The term polymerizable moiety refers to ethylenically unsaturated moieties known in the art which are capable of reaction with another compound (for example by a free radical mechanism), such as but not limited to, acrylate and methacrylate moieties. For example A can have the structure —(CH$_2$)$_n$—OC(O)—CRH=CH$_2$, wherein n is an integer from 1 to 10 and R is H or lower alkyl. Yet another exemplary polymerizable moiety can be a maleimide moiety

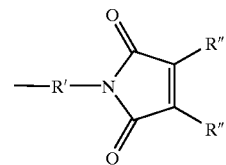

wherein:
R' is selected from the group consisting of —(CH$_2$)$_n$—, wherein n is an integer from 0 to 10, optionally substituted with one or more heteroatom in the —CH$_2$— chain; and
each R" is independently selected from the group consisting of hydrogen, lower alkyl and halogen.

The term oligomeric moiety refers to a moiety including two or more monomer units (dimer, trimer, etc.) such as but not limited to an C2C20 alkylene or polyalkylene polyol, wherein hydroxy groups of the polyol are optionally alkylated, and preferably an alkylene or polyalkylene polyol derived from ethylene glycol. Other suitable oligomer moieties include C2-C20 alkylene or polyalkylene moieties end capped with trihaloalkyl, and optionally substituted with one or more halogen atoms along the chain, preferably fluorine. Other exemplary oligomeric moieties include C2-C20 alkylene or polyalkylene moieties including carbonate groups and end capped with lower alkyl.

In one embodiment of the invention, each A of the compound of Formula (I) is lower alkyl, preferably methyl or ethyl, with the proviso that no more than three As are the same. In another embodiment of the invention at least one A is lower alkyl, preferably methyl or ethyl, and at least one other A is a polymerizable moiety or an oligomeric moiety.

Exemplary compounds in accordance with Formula I include without limitation:

4,4'-bis(methylethylamino)benzophenone.

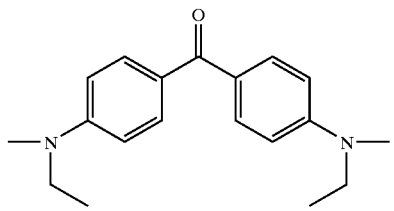

4-(dimethylamino)-4'-(methylethylamino)benzophenone

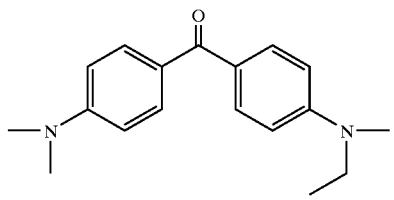

4-(diethylamino)-4'-(methylethylamino)benzophenone

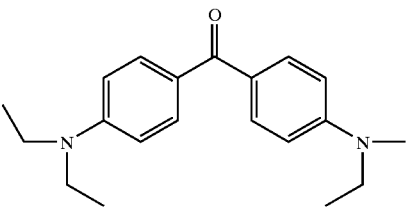

4,4'-bis(methylethanolamino)benzophenone

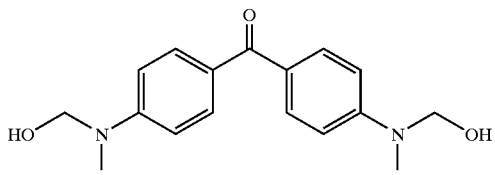

4,4'-bis(methylmethylacrylateamino)benzophenone

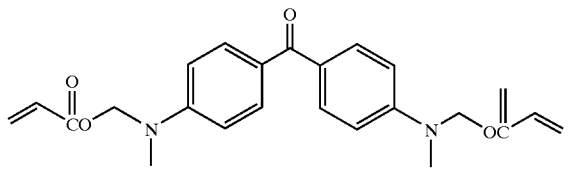

4,4'-bis(maleimideamino)benzophenone

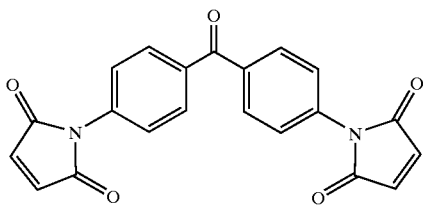

-continued
4-(methylethylamino)-4'-(aliphatic maleimideamino)benzophenone

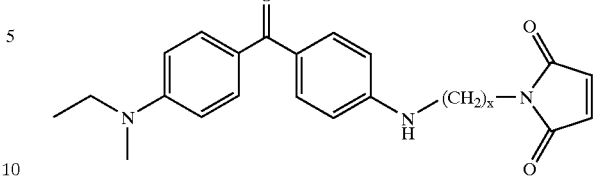

wherein x is an integer from 1 to 20; and the like.

Advantageously the compounds of the invention, such as MEAB, are appropriately substituted to possess UV spectra with significant absorption bands between 250 and 350 nanometers (nm), more preferably between 290 and 325 nm, and most preferably about 308 nm.

In another embodiment of the invention, photopolymerizable compositions are provided which include a compound of Formula (I) above as a photoinitiator. As used herein, and as will be appreciated by the skilled artisan, the term photopolymerizable composition refers to compositions which harden or cure upon exposure to radiation.

Generally the compositions of the invention include ethylenically unsaturated compounds, including monomers, oligomers, polymers, prepolymers, resinous materials, optionally dispersed or dissolved in a suitable solvent that is copolymerizable therewith, and mixtures thereof, which are photopolymerizable when exposed to a source of ultraviolet ("UV") radiation. As will be appreciated by the skilled artisan, the photopolymerizable compounds can be monofunctional, or can include two or more terminal polymerizable ethylenically unsaturated groupings per molecule.

Exemplary photopolymerizable compounds or precursors include, but are not limited to, reactive vinyl monomers, including acrylic monomers, such as acrylic and methacrylic acids, and their amides, esters, salts and corresponding nitriles. Suitable vinyl monomers include, but are not limited to, methyl acrylate, ethyl acrylate, n- or tert-butylacrylate, isooctyl acrylate, methyl methacrylate, ethylmethacrylate, 2-ethylhexyl methacrylate, butylacrylate, isobutyl methacrylate, the corresponding hydroxy acrylates, i.e., hydroxy ethylacrylate, hydroxy propylacrylate, hydroxy ethylhexyl methacrylate, glycol acrylates, i.e., ethylene glycol dimethacrylate, hexamethylene glycol dimethacrylate, the allyl acrylates, i.e., allyl methacrylate, diallyl methacrylate, the epoxy acrylates, i.e., glycidyl methacrylate, and the aminoplast acrylates, i.e., melamine acrylate. Others such as vinyl acetate, vinyl and vinylidene halides and amides, i.e., methacrylamide, acrylamide, diacetone acrylamide, butadiene, styrene, vinyl toluene, and the like are also included. Prepolymers include acrylated epoxides, polyesters and polyurethanes, and are typically combined with a suitable monomer for viscosity control. The photopolymerizable compounds may be polymerized to form homopolymers or copolymerized with various other monomers.

The photopolymerizable compound can be present in the compositions of the invention in amounts between about 99.8 and about 90 percent by weight of the composition, preferably between about 99.5 and about 95 percent by weight.

In this aspect of the invention, the compounds of Formula (I) act as photopolymerization initiators. The compounds of Formula (I) are added to the photopolymerizable compound in an amount sufficient to initiate polymerization thereof upon exposure to ultraviolet radiation. Preferably the compounds of Formula (I) are present in the photopolymerizable composition an amount between about 0.2 and 10 parts by weight of the composition, and more preferably between about 0.5 and about 5 parts by weight, depending on the specific application.

The use of the compounds of Formula (I) can exhibit photoinitiation activity similar to that of Michler's Ketone, but unexpectedly also have greatly reduced toxicity.

The compositions of the invention can also include any of the various pigments, organic and inorganic, known in the art. Exemplary pigments include, but are not limited to, opacifying pigments such as zinc oxide, titania, e.g., anatase and rutile; basic lead sulfate, magnesium silicate, silica, clays, wollastonite, talcs, mica, chromates, iron pigments, wood fluor, microballons, hard polymer particles, glass fiber or flake. Pigments can be present in the compositions of the invention in conventional amounts, i.e., between about 1 and about 40 percent by weight.

It can also be advantageous to also include as a component of the compositions of the invention a coinitiator or synergist, that is, a molecule which serves as a hydrogen atom donor. Coinitiators or synergists are known in the art, and are typically alcohols, tertiary amines or ethers which have available hydrogens attached to a carbon adjacent to a heteroatom. Such co-initiators are typically present in an amount between about 0.2 and about 25 percent by weight. Suitable compounds include triethanolamine, methyldiethanolamine, ethyldiethanolamine and esters of dimethylamino benzoic acid. These compounds behave as co-initiators or accelerators for the primary photoinitiators and can increase the efficiency and speed of the polymerization process.

In addition, the compositions of the present invention may contain polymerization inhibitors, fillers, ultraviolet absorbers and organic peroxides.

The compositions of the invention can be applied or deposited to a surface of a substrate using conventional techniques and apparatus. The composition can be applied as a substantially continuous film; alternatively, the composition can be applied in a discontinuous pattern. Usually the compositions of the invention are fluid at ordinary operating temperatures (between ambient and up to about 60° C.).

The thickness of the deposited composition can vary, depending upon the desired thickness of the resultant cured product. Advantageously, the composition is applied to the substrate surface in an amount sufficient to provide a cured coating having a thickness between about 1 micron and about 250 mils.

Typically, the substrate is coated with the uncured photopolymerizable composition and passed under an ultraviolet providing light beam by a conveyer moving at predetermined speeds. The substrate to be coated can be, for example, metal, mineral, glass, paper, plastic, fabric, ceramic, and the like.

The active energy beams used in accordance with the present invention may be ultraviolet light or may contain in their spectra both visible and ultraviolet light. The polymerization may be activated by irradiating the composition with ultraviolet light using any of the techniques known in the art for providing ultraviolet radiation, i.e., in the range of 240 nm and 420 nm ultraviolet radiation. The radiation may be natural or artificial, monochromatic or polychromatic, incoherent or coherent and should be sufficiently intense to activate the photoinitiators of the invention and thus the polymerization. Conventional radiation sources include fluorescent lamps, mercury, metal additive and arc lamps. Coherent light sources are the pulsed nitrogen, xenon, argon ion- and ionized neon lasers whose emissions fall within or overlap the ultraviolet or visible absorption bands of the compounds of the invention. In one embodiment of the invention, the composition including the compounds of the invention is exposed to ultraviolet radiation having a wavelength of about 240 to about 420 nm.

Figure 2:
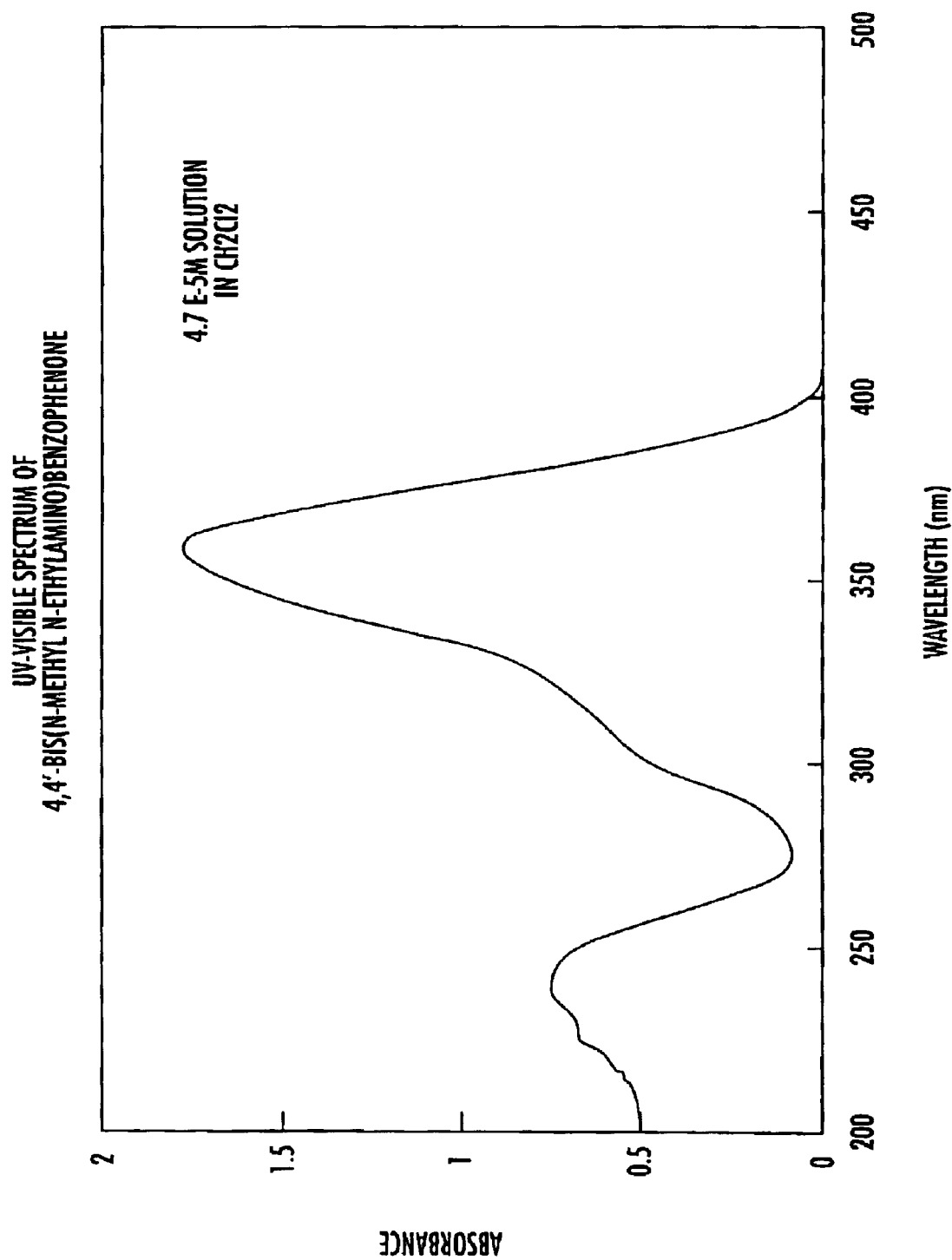
FIG. 2 illustrates the UV absorption of 4,4'-bis(methylethylamino)benzophenone (MEAB).

As noted above, advantageously the compounds of the invention are appropriately substituted to possess UV spectra with significant absorption bands between 250 and 350 nm and in particular between 290 and 325 nm. Accordingly, the compounds can be irradiated with a narrow wavelength band, high pressure fill UV curing lamp known as an excimer lamp with spectral emphasis in the 250 to 350 nm range, and in particular with its peak emission wavelength at or near 308 nm, as described in U.S. Pat. No. 5,504,391, the entire disclosure of which is hereby incorporated in its entirety. The compounds of Formula (I) show a significantly elevated level of reactivity at these wavelengths. Because of the increased level of activity the photoinitiator can be used in considerably lower amounts. For example, when the compounds of the invention are used with an excimer lamp versus a medium pressure mercury lamp, only about one-fourth of the amount of photoinitiator can be required to give equivalent cure speeds. IN addition, when the same concentration of photoinitiator is used with both an excimer and a medium pressure mercury lamp the excimer lamp can provide greatly increased cure speeds. UV Spectra are provided for the excimer lamp and for MEAB in FIGS. 1 and 2, respectively.

When polymerized by exposure to UV radiation, the compositions of the invention give a substantially tack-free product which is durable for ordinary handling. The compositions of the invention are useful in any of the types of applications known in the art for photopolymerizations, including as a binder for solids to yield a cured product in the nature of a paint, varnish, enamel, lacquer, stain or ink. The compositions are particularly useful in the production of photopolymerizable surface coatings in printing processes, such as lithographic printing, screen printing, and the like.

The compounds of the invention can be prepared from an aniline compound which may be substituted at any position except the 4 position. The nitrogen atom of the aniline can be substituted using techniques known in the art. For example, the aniline can be alkylated using known techniques. In this regard, the aniline can be converted to an N-ethylaniline by reductive alkylation with acetaldehyde by methods reviewed by Rylander in "Catalytic Hydrogenation over Platinum Metals." The N-ethylaniline may be converted to an N-ethyl, N-methylaniline by subsequent reductive alkylation with formaldehyde. These N-alkylations may also be performed with alcohol reagents by methods known in the art. The order of the N-alkylations may also be reversed in order to firstly form the N-methyl and secondly form the N-ethyl, N-methyl intermediate. The N-ethyl, N-methylaniline may be converted to the 4,4'-bis (methylethylamino)benzophenone by reaction with phosgene in the method of Michler disclosed in Chemische Berichte in the year 1876, p. 1914. This synthesis is described in detail in the following example of the conversion of N-ethylaniline, which is commercially available from First Chemical Corporation, to the photoinitiator 4,4'-bis(methylethylamino)benzophenone.

Alternative synthetic routes are disclosed in Japanese Kokai 08-12630 published Jan. 16, 1996 and in German patent 2226039, which teach the formation of a diphenylmethane and subsequent oxidation to form the benzophenone. For example, to prepare MEAB, N-ethylaniline can be reacted with formaldehyde with palladium catalyst to produce N-ethylmethyl aniline, which can be reacted with formaldehyde to give 4,4'-bis(ethylmethylamino)diphenyl methane, which is oxidized using a suitable oxidizing agent, such as chloranil/sodium chlorite. Yet another alternative route is amination of 4,4'-bis(chloro)benzophenone with methylethylamine by the method disclosed in U.S. Pat. No. 2,231,067.

The nitrogen atoms can alternatively be hydroxylated as known in the art, or one can start with hydroxy substituted aniline compounds, such as N-alkyl, N'-hydroxyalkyl anilines, commercially available, for example, from First Chemical Corporation. The hydroxyl functionality is reacted with suitable reagents as known in the art to provide the desired functionality. For example, a hydroxyl functionality can be reacted with a sulfonyl halide to provide sulfonyl groups. A hydroxyl functionality can alternatively be reacted with acryloyl halide to provide an acrylate group.

In yet another embodiment of the invention, compounds having at least one maleimide unit can be prepared according to techniques known in the art. For example, a suitably attached aromatic amine can be reacted with maleic anhydride (or a substituted maleic anhydride such as citraconic anhydride) in a polar solvent to provide the amic acid. This is followed by an acid catalyzed ring closure to form the imide. Compounds having maleimide functional groups are described in pending U.S. provisional application Serial No. 60/047,729; pending U.S. application Ser. No. 08/917,024; Z. Y. Wang, Synthetic Comm. 20(11) 1607–1610 (1990); P. O. Tawnet et al., J.Org.Chem. 26, 15 (1961); and U.S. Pat. No. 2,542,145, the entire disclosure of each of which is hereby incorporated by reference. See also U.S. Pat. Nos. 5,629,356 and 5,468,904 and WO 96/33156, the entire disclosure of each of which is also incorporated by reference, which are directed to compounds which have polymerizable or oligomeric moieties incorporated therein.

Other compounds which can be converted to a benzophenone include, but are not limited to, N-ethyl-m-toluidine, o-toluidine, m-toluidine, 3-propylaniline, 2,3-dimethylaniline, 2,5-dimethylaniline, 2,6-dimethylaniline, 3,5-dimethylaniline, 2-cyclopentylaniline, o-anisidine, m-anisidine, 2-(methylsulfonyl)aniline, 2-fluoroaniline, 2-chloroaniline, 3-chloroaniline, 2,6-dichloroaniline, 2,3,5, 6-tetrachloroaniline, 2-(trifluoromethyl)aniline, 3-(trifluoromethyl)aniline, 2-(trifluoromethoxy)aniline, 2-[(trifluoromethyl)thio]aniline, and the like.

The present invention will be further illustrated by the following non-limiting examples.

EXAMPLE 1

Synthesis of 4,4'-Bis(methylethylamino) benzophenone (MEAB)

Ethyl-aniline is methylated by reductive alkylation with formaldehyde using isopropyl alcohol as a solvent at 100° C. under 120 psi of $H_2$. After the solvent is stripped the product ethylmethylaniline (NEMA) is purified by distillation at 120° C. at a pressure of 21 mm mercury (Hg). NEMA (80 g, 0.59 mol) is charged to a vessel fitted with a dry-ice condenser and is heated to 50 –60° C. Phosgene is transferred from a cylinder to a calibrated trap placed in dry-ice. After condensing 10 mL (14.3 g, 0.145 mol), the trap was connected to the vessel containing NEMA and the phosgene was added over 1 hour. After the addition was complete, the mixture was heated to 120° C. and held at this temperature for 1 hour. The mixture was cooled to 50–60° C. before 11 g (0.275 mol) of NaOH dissolved in 100 mL of water was added to hydrolyze the unreacted acid chloride. The resulting mixture was then extracted with two 100 mL portions of toluene. The product 4,4'-bis(methylethylamino) benzophenone (MEAB) was purified by chromatography on silica gel using toluene as an eluent followed by recrystallization from methylene chloride/hexane. Several grams of highly pure MEAB were obtained. No impurities were detectable by NMR; m.p. 122–124° C. NMR, IR and mass spectra were consistent with the proposed structure.

EXAMPLE 2

Use of MEAB as Photoinitiator

Michler's Ketone (also tetramethyl Michler's Ketone or TMMK), tetraethyl Michler's Ketone (also 4,4'-bis (diethylamino)benzophenone or TEMK), and MEAB were tested in curing hexanediol diacrylate compositions. The composition included 1% isopropylthioxanthone, 2% ethyl 4-N,N-dimethylaminobenzoate, 4% benzophenone, 1% aminobenzophenone compound, and the balance hexanediol diacrylate. The composition was applied as a 0.15 inch film to a substrate and cured with a Fusion UV Systems "H" bulb with 600 Watts/inch power with a belt speed of 55 feet per minute. MEAB and TMMK both required 10 passes under the lamp to obtain a well-cured hard polymer, and TEMK required 25 passes. This illustrates that MEAB and TMMK have approximately the same activity, and both are much superior to the tetraethyl compound.

EXAMPLE 3

Comparative Mutagenicity of TMMK, TEMK and MEAB

Michler's ketone (TMMK) is listed by the National Toxicology Program as "reasonably anticipated to be a carcinogen" based on the results of cancer studies in rats and mice. Seventh Annual Report on Carcinogens, U.S. Dept. Health Human Services, p. 259, 1994. Based on comparisons of mutagenicity studies with animal cancer studies, mutagens are more likely to cause cancer, to produce tumors in multiple organs, and to affect multiple species. Gold, L. S. et al., Mutat. Res. 286, 75–100 (1993).

Mutagenicity can be measured by a variety of assays. The most commonly used method is the Salmonella/ Mammalian-Microsome Reverse Mutation Screening Assay (Ames Test), which commonly uses four or five strains of Salmonella bacteria to detect different types of mutations.

Michler's Ketone has been tested in the Ames Test a number times. Scribner, J. D. et al. Cancer Lett. 9, 117–121 (1980); McCarthy, D. J. et al. Mutat. Res. 119, 7–14 (1983); Dunkel, V. C. et al., Environ. Mutagen. 7 (Suppl. 5), 1–248 (1985); Zeiger, E. et al., Environ. Mol. Mutagen. 19 (Suppl. 21), 2–141 (1992). In this assay, the bacterial strain which was consistently found to have mutations when adequate concentrations of test material were used was strain *Salmonella typhimurium* tester strain TA98, with added mammalian metabolic activation. Dunkel, V. C. et al., Environ. Mutagen. 7 (Suppl. 5), 1–248 (1985); Zeiger, E. et al., Environ. Mol. Mutagen. 19 (Suppl. 21), 2–141 (1992).

TMMK, TEMK and MEAB were evaluated for the ability to induce reverse mutations at the histidine locus in the genome of a specific *Salmonella typhimurium* tester strain in the presence of an exogenous metabolic activation system of mammalian microsomal enzymes derived from Aroclor™-induced rat liver (S9). The tester strain used in the mutagenicity assay was *Salmonella typhimurium* tester strain TA98 with added activation. The assay was conducted using eight doses of the test article, along with the appropriate vehicle and positive controls in the presence of S9 mix (S9 homogenate was purchased from Molecular Toxicology, Inc., Annapolis, Md. 21401, Batch 0646, 43.4 mg of protein per ml). Positive controls were also plated in the absence of S9 mix. All doses of test article, vehicle, and positive controls were plated in triplicate.

1. Test Article Handling

The test article TMMK was stored at room temperature. Acetone (CAS# 67-64-1, Fisher Scientific Co., Lot 961140) was used as the vehicle. At 20 mg per ml, which was the most concentrated stock solution which could be prepared, the test article formed a clear, light yellow solution. The test article remained a solution in all succeeding dilutions prepared for the mutagenicity assay. The maximum aliquot of acetone which can be used in the test system is 200 µl. Thus, the maximum concentration which could be tested was 4,000 µg per plate. The test article and vehicle controls were plated using a 200 µl plating aliquot. Positive control articles were plated using 50 µl plating aliquot.

The test article TEMK was stored at room temperature. Acetone (CAS# 67-64-1, Fisher Scientific Co., Lot 961140) was used as the vehicle. At 100 mg per ml, which was the most concentrated stock solution prepared, the test article formed a clear, yellow solution. The test article remained a solution in all succeeding dilutions prepared for the mutagenicity assay. The test article, vehicle controls and positive control articles were plated using a 50 µl plating aliquot.

The test article MEAB was stored at room temperature. Acetone (CAS# 67-64-1, Fisher Scientific Co., Lot 961140) was used as the vehicle. At 25 mg per ml, which was the most concentrated stock solution prepared, the test article formed a clear, light yellow solution. The test article remained a solution in all succeeding dilutions prepared for the mutagenicity assay. The test article and vehicle controls were plated using a 200 µl plating aliquot. Positive control articles were plated using a 50 µl plating aliquot.

2. Mutagenicity Assay

The mutagenicity assay results for TMMK, TEMK, and MEAB are presented in Table 1. The data are presented as individual plate counts along with a mean and standard deviation.

The results of the Salmonella/Mammalian-Microsome Reverse Mutation Screening Assay (Ames Test) indicate that TMMK did cause a positive (3.9-fold) increase in the number of revertants per plate with tester strain TA98 in the presence of S9 mix. Test articles TEMK and MEAB did not cause a positive increase in the number of revertants per plate with tester strain TA98 in the presence of S9 mix. Of the three test materials, only TMMK was mutagenic. For aromatic amino or nitro compounds such as these test materials, very few which were not mutagenic in the Ames test have been found to cause tumors in animal cancer studies. Ashby, J. and Tennant, R. W., Mutat. Res. 257, 229–306 (1991). Therefore, these results suggest that MEAB has a lower potential to cause tumors than TMMK.

TABLE 1

MUTAGENICITY ASSAY RESULTS
INDIVIDUAL PLATE COUNTS
REVERTANTS PER PLATE

| | COMPOUND | | | | | | | | | | | |
|---|---|---|---|---|---|---|---|---|---|---|---|---|
| | TMMK | | | | TEMK | | | | MEAB | | | |
| SAMPLE | 1 | 2 | 3 | BACK GROUND LAWN* | 1 | 2 | 3 | BACK GROUND LAWN* | 1 | 2 | 3 | BACK GROUND LAWN* |
| MICROSOMES: Rat Liver VEHICLE CONTROL TEST ARTICLE (DOSE/PLATE) | 10 | 22 | 30 | 1 | 16 | 36 | 11 | 1 | 9 | 20 | 30 | 1 |
| 3.33 µg | 14 | 29 | 24 | 1 | 22 | 22 | 30 | 1 | 13 | 21 | 22 | 1 |
| 10.0 µg | 9 | 19 | 19 | 1 | 30 | 24 | 20 | 1 | 25 | 28 | 11 | 1 |
| 33.3 µg | 21 | 35 | 37 | 1 | 13 | 23 | 19 | 1 | 24 | 25 | 24 | 1 |
| 100 µg | 16 | 12 | 22 | 1sp | 28 | 26 | 24 | 1 | 20 | 18 | 20 | 1sp |
| 333 µg | 18 | 23 | 12 | 1mp | 20 | 17 | 19 | 1sp | 21 | 31 | 19 | 1mp |
| 1000 µg | 35 | 26 | 33 | 1mp | 32 | 23 | 17 | 1mp | 36 | 23 | 21 | 1mp |
| 3330 µg | 78 | 82 | 78 | 6mp | 27 | 15 | 25 | 1mp | 27 | 14 | 17 | 1hp |
| 4000 µg | 80 | 70 | 93 | 6mp | NT | NT | NT | — | NT | NT | NT | — |
| 5000 µg | NT | NT | NT | — | 27 | 19 | 19 | 1mp | 23 | 23 | 27 | 1hp |
| POSITIVE CONTROL** | 1053 | 920 | 932 | 1 | 1264 | 1032 | 1133 | 1 | 1196 | 1225 | 1226 | 1 |

**TA98 2-aminoanthracene 2.5 µg/plate
*Background Lawn Evaluation Codes:
1 = normal
2 = slightly reduced
3 = moderately reduced
4 = extremely reduced
5 = absent
6 = obscured by precipitate
sp = slight precipitate
mp = moderate precipitate (requires hand count)
hp = heavy precipitate (requires hand count)
NT = Not tested.

TABLE 2

MUTAGENICITY ASSAY RESULTS SUMMARY
MEAN REVERTANTS PER PLATE WITH STANDARD DEVIATION

| | COMPOUND | | | | | | | | |
|---|---|---|---|---|---|---|---|---|---|
| | TMMK | | | TEMK | | | MEAB | | |
| DOSE/PLATE | MEAN | S.D. | BACKGROUND LAWN* | MEAN | S.D. | BACKGROUND LAWN* | MEAN | S.D. | BACKGROUND LAWN* |
| MICROSOMES: Rat Liver VEHICLE CONTROL DOSE/PLATE | 21 | 10 | 1 | 21 | 13 | 1 | 20 | 11 | 1 |
| 3.33 μg | 22 | 8 | 1 | 25 | 5 | 1 | 19 | 5 | 1 |
| 10.0 μg | 16 | 6 | 1 | 25 | 5 | 1 | 21 | 9 | 1 |
| 33.3 μg | 31 | 9 | 1 | 18 | 5 | 1 | 24 | 1 | 1 |
| 100 μg | 17 | 5 | 1sp | 26 | 2 | 1 | 19 | 1 | 1sp |
| 333 μg | 18 | 6 | 1mp | 19 | 2 | 1sp | 24 | 6 | 1mp |
| 1000 μg | 31 | 5 | 1mp | 24 | 8 | 1mp | 27 | 8 | 1mp |
| 3330 μg | 79 | 2 | 6mp | 22 | 6 | 1mp | 19 | 7 | 1hp |
| 4000 μg | 81 | 12 | 6mp | NT | — | — | NT | — | — |
| 5000 μg | NT | — | — | 22 | 5 | 1mp | 24 | 2 | 1hp |
| POSITIVE CONTROL** | 968 | 74 | 1 | 1143 | 116 | 1 | 1216 | 17 | 1 |

**TA98 2-aminoanthracene 2.5 μg/plate
*Background Lawn Evaluation Codes.
1 = normal
2 = slightly reduced
3 = moderately reduced
4 = extremely reduced
5 = absent
6 = obscured by precipitate
sp = slight precipitate
mp = moderate precipitate (requires hand count)
hp = heavy precipitate (requires hand count)
NT = Not tested.

The foregoing examples are illustrative of the present invention and are not to be construed as limiting thereof. The invention is defined by the following claims, with equivalents of the claims to be included therein.

That which is claimed:

1. A substantially non-mutagenic photopolymerizable composition which is substantially free of epoxy resin and comprising a photopolymerizable compound and a substantially non-mutagenic photoinitiator having photoimtiation activity sinular to that exhibited by 4,4'-bis(dimethylamino) benzophenone under similar conditions, said photoinitiator having the formula

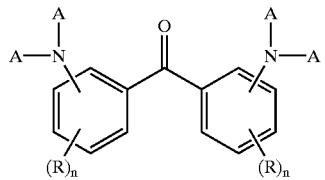

wherein:
each A is independently selected from the group consisting of hydrogen, lower alkyl, cycloalkyl, aryl, lower alkanol, lower alkoxy, halogen, sulfonyl, ailcylsulfonyl, trihaloalkyl, trihaloalkoxy, trihaloalkylthio, polynierizable moiety —(CH$_2$)$_{n'}$—OC(O)—CR'H=CH$_2$, wherein n' is an integer from 1 to 10 and R' is H or lower alkyl, polymerizable maleimick moiety, and oligomeric moiety, with the proviso that no more than three A are the same lower alkyl;
each R is independently selected from the group consisting of hydrogen, lower alkyl, cycloalkyl, aryl, lower alkanol, lower alkoxy, halogen, sulfonyl, alkylsulfonA, trihaloalkyl, trilialoalkoxy, trihaloallcylthio, polyinerizable moiety, and oligomeric moiety; and
n is an integer from 1 to 4.

2. The composition of claim 1, wherein each A is independently lower alkyl.

3. The composition of claim 2, wherein two As are methyl and two As are ethyl.

4. The composition of claim 2, wherein three As are methyl and one A is ethyl.

5. The composition of claim 2, wherein three As are ethyl and one A is methyl.

6. The composition of claim 1, wherein said photoinitiator is selected from the group consisting of 4,4'-bis(methylethylamino)benzophenone, 4-(dimethylamino)-4'-(methylethylamino)benzophenone, 4-(diethylamino)-4'-(methylethylamino)benzophenone, 4,4'-bis(methylethanolamino)benzophenone, 4,4'-bis(methylmethylacrylateamino)benzophenone, 4,4'-bis(maleimideamino)benzophenone, and 4-(methylethylamino)-4'-(aliphatic maleimideamino)benzophenone having the formula

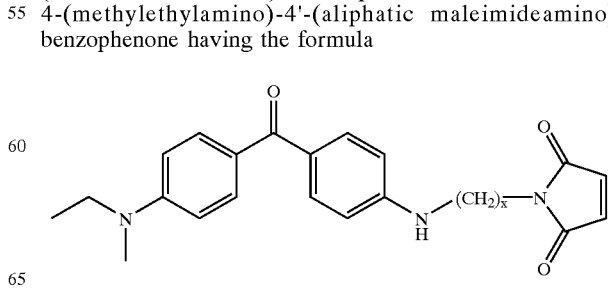

wherein x is an integer from 1 to 20, and mixtures thereof.

7. The composition of claim 1, wherein each R is hydrogen.

8. The composition of claim 1, wherein the photopolymerizable compound comprises acrylate.

9. The composition of claim 1, wherein said photopolymerizable compound is the majority component of said composition.

10. The composition of claim 1, wherein the photopolymerizable compound is selected from the group consisting of methyl acrylate, ethyl acrylate, n-butylacrylate, tert-butylacrylate, isooctyl acrylate, methyl methacrylate, ethyhnethacrylate, 2-ethyihexyl methacrylate, butylacrylate, isobutyl methacrylate, corresponding hydroxy acrylates, glycol acrylates, allyl acrylates, epoxy acrylates, aniinoplast acrylates, vinyl acetate, vinyl halides, vinylidene halides, vinylamides, vinylidene amides, butadiene, styrene, and vinyl toluene.

11. The composition of claim 1, wherein the photopolymerizable compound is present in an amount of from about 90.0 percent by weight to about 99.8 percent by weight in the composition.

12. The composition of claim 11, wherein the photopolymerizable compound is present in an amount of from about 95.0 percent by weight to about 99.5 percent by weight in the composition.

13. The composition of claim 1, wherein the photoinitiator is present in an amount of from about 0.2 to about 10 parts by weight of the composition.

14. The composition of claim 13, wherein the photoinitiator is present in an amount of from about 0.5 to about 5 parts by weight.

15. The composition of claim 1 further comprising a pigment.

16. The composition of claim 15, wherein the pigment is selected from the group consisting of zinc oxide, titania, basic lead sulfate, magnesium silicate, silica, clays, wollastonite, talcs, mica, chromates, iron pigments, wood fluor, microballons, hard polymer particles, glass fiber and glass flake.

17. The composition of claim 15, wherein the pigment is present in an amount of from about 1 to about 40 percent by weight in the composition.

18. A substantially non-mutagenic photopolymerizable composition which is substantially free of epoxy resin and comprising a photopolymerizable compound and a substantially non-mutagenic photoinitiator having photoinitiation activity similar to that exhibited by 4.4'-bis(dimethylamino) benzophenone under similar conditions, said photoinitiator having the formula

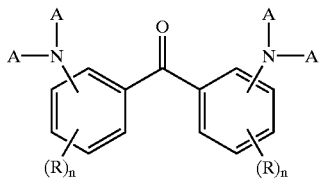

wherein:
each A is independently selected from the group consisting of hydrogen, lower alkyl, cycloalkyl, aryl, lower alkanol, lower alkoxy, halogen, sulfonyl, ailcylsulfonyl, trihaloalkyl, trihaloalkoxy, trihaloalkylthio, polynierizable moiety —(CH$_2$)$_{n'}$—OC(O)—CR'H=CH$_2$, wherein n' is an integer from 1 to 10 and R' is H or lower alkyl, polymerizable maleimick moiety, and oligomeric moiety, with the proviso that no more than three A are the same lower alkyl;

each R is independently selected from the group consisting of hydrogen, lower alkyl, cycloalkyl, aryl, lower alkanol, lower alkoxy, halogen, sulfonyl, alkylsulfonA, trihaloalkyl, trilialoalkoxy, trihaloallcylthio, polyinerizable moiety, and oligomeric moiety; and n is an integer from 1 to 4 said composition further comprising at least one component selected from the group consisting of polymerization inhibitors, fillers, ultraviolet absorbers and organic peroxides.

19. A substantially non-mutagenic photopolymerizable composition which is substantially free of epoxy resin and comprising a photopolymerizable compound and a substantially non-mutagenic photoinitiator having photoinitiation activity similar to that exhibited by 4.4'-bis(dimethylamino) benzophenone under similar conditions, said photoinitiator having the formula

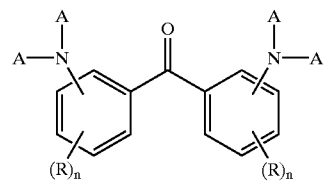

wherein:
each A is independently selected from the group consisting of hydrogen, lower alkyl, cycloalkyl, aryl, lower alkanol, lower alkoxy, halogen, sulfonyl, ailcylsulfonyl, trihaloalkyl, trihaloalkoxy, trihaloalkylthio, polynierizable moiety —(CH$_2$)$_{n'}$—OC(O)—CR'H=CH$_2$, wherein n' is an integer from 1 to 10 and R' is H or lower alkyl, polymerizable maleimick moiety, and oligomeric moiety, with the proviso that no more than three A are the same lower alkyl;

each R is independently selected from the group consisting of hydrogen, lower alkyl, cycloalkyl, aryl, lower alkanol, lower alkoxy, halogen, sulfonyl, alkylsulfonyl, trihaloalkyl, trilialoalkoxy, trihaloallcylthio, polyinerizable moiety, and oligomeric moiety; and n is an integer from 1 to 4 said composition further comprising a coinitiator.

20. The composition of claim 19, wherein the coinitiator is selected from the group consisting of triethanolamine, methyl-diethanolamine, ethyldiethanolamine and esters of dimethylamino benzoic acid.

21. The composition of claim 19, wherein the coinitiator is present in an amount of from about 0.2 to about 25 percent by weight of the composition.

22. A substantially non-mutagenic photopolymerizable composition which is substantially free of epoxy resin and comprising a photopolymerizable acrylate compound and a substantially non-mutagenic photoinitiator having photoinitiation activity similar to that exhibited by 4,4'-bis(dimethylamino)benzophenone under similar conditions, said photoinitiator selected from the group consisting of 4,4'-bis(methylethylamino)benzophenone, 4-(dimethylamino)-4'-(methylethylamino)benzophenone, 4-(diethylamino)-4'-(methylethylamino)benzophenone, 4,4'-bis(methylethanolamino)benzophenone, 4,4'-bis(methylmethylacrylateamino)benzophenone, 4,4'-bis(maleimideamino)benzophenone, and 4-(methylethylamino)-4'-(aliphatic maleimideamino)benzophenone having the formula

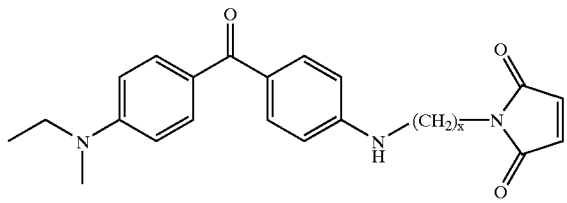

wherein x is an integer from 1 to 20, and mixtures thereof.

23. The composition of claim 22, wherein said photopolymerizable acrylate compound is the majority component of said composition.

24. The composition of claim 22, wherein the photoinitiator is 4,4'-bis(methylethylamino) benzophenone.

25. The composition of claim 22, wherein the photopolymerizable compound is selected from the group consisting of methyl acrylate, ethyl acrylate, n-butylacrylate, tert-butylacrylate, isooctyl acrylate, methyl methacrylate, ethylmethacrylate, 2-ethyihexyl methacrylate, butylacrylate, isobutyl methacrylate, corresponding hydroxy acrylates, glycol acrylates, allyl acrylates, epoxy acrylates and aminoplast acrylates.

26. The composition of claim 22, wherein the photopolymerizable compound is present in an amount of from about 90.0 percent by weight to about 99.8 percent by weight in the composition.

27. The composition of claim 26, wherein the photopolymerizable compound is present in an amount of from about 95.0 percent by weight to about 99.5 percent by weight in the composition.

28. The composition of claim 22, wherein the photoinitiator is present in an amount of from about 0.2 to about 10 parts by weight of the composition.

29. The composition of claim 28, wherein the photoinitiator is present in an amount of from about 0.5 to about 5 parts by weight.

30. The composition of claim 22 further comprising a pigment.

31. The composition of claim 30, wherein the pigment is selected from the group consisting of zinc oxide, titania, basic lead sulfate, magnesium silicate, silica, clays, wollastonite, talcs, mica, chromates, iron pigments, wood fluor, microballons, hard polymer particles, glass fiber and glass flake.

32. The composition of claim 30, wherein the pigment is present in an amount of from about 1 to about 40 percent by weight in the composition.

33. A substantially non-mutagenic phoiopolymerizable composition which is substantially free of epoxy resin and comprising a photopolymerizable acrylate compound and a substantially non-mutagenic photoinitiator having photoinitiation activity similar to that exhibited by 4,4'-bis(dimethylamino)benzophenone under similar conditions said photoinitiator selected from the group consisting of 4,4'-bis(methylethylamino)benzophenone, 4-(dimethylamino-4'-(methylethylamino)benzophenone, 4-(diethylamino)-4'-(methylethylamino)benzophenone, 4,4'-bis(methylethylamino) benzophenone, 4,4'-bis(methylmethylacrylatcamino)benzophenone, 4,4'-bis(maleimideamino) benzophenone, and 4-(methylethylamino)-4'-(aliphatic malcimideamino) benzophenone having the formula

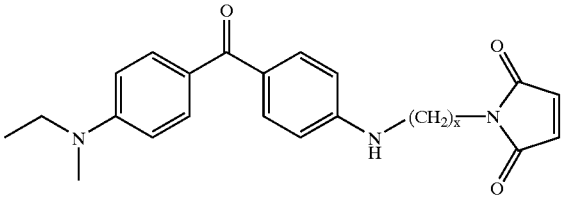

wherein x is an integer from 1 to 20, and mixtures thereof
said composition further comprising at east one component selected from the group consisting of polymerization inhibitors, fillers, ultraviolet absorbers and organic peroxides.

34. A substantially non-mutagenic phoiopolymerizable composition which is substantially free of epoxy resin and comprising a photopolymerizable acrylate compound and a substantially non-mutagenic photoinitiator having photoinitiation activity similar to that exhibited by 4,4'-bis(dimethylamino)benzophenone under similar conditions said photoinitiator selected from the group consisting of 4,4'-bis(methylethylamino)benzophenone, 4-(dimethylamino-4'-(methylethylamino)benzophenone, 4-(diethylamino)-4'-(methylethylamino)benzophenone, 4,4'-bis(methylethylamino) benzophenone, 4,4'-bis(methylmethylacrylatcamino)benzophenone, 4,4'-bis(maleimideamino) benzophenone, and 4-(methylethylamino)-4'-(aliphatic malcimideamino) benzophenone having the formula

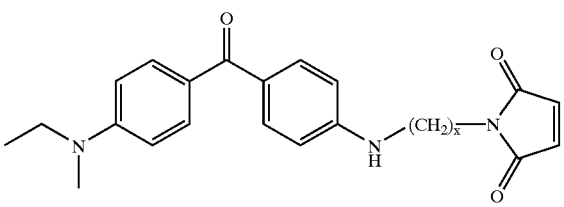

wherein x is an inteaer from 1 to 20 and mixtures thereof,
said composition further comprising a coinitiator.

35. The composition of claim 34, wherein the coinitiator is selected from the group consisting of triothanolamine, methyl-diethanolamine, ethyldiethanolamine and esters of dimethylamino benzoic acid.

36. The composition of claim 35, wherein the coinitiator is present in an amount of from about 0.2 to about 25 percent by weight of the composition.

* * * * *

UNITED STATES PATENT AND TRADEMARK OFFICE
CERTIFICATE OF CORRECTION

PATENT NO. : 6,797,841 B2
DATED : September 28, 2004
INVENTOR(S) : Santobianco et al.

It is certified that error appears in the above-identified patent and that said Letters Patent is hereby corrected as shown below:

Column 13,
Line 60, "ailcylsulfonyl" should read -- alkylsulfonyl --;
Line 61, "polynierizable" should read -- polymerizable --;
Line 63, "maleimick" should read -- maleimide --.

Column 14,
Line 35, "alkylsulfonA" should read -- alkylsulfonyl --;
Line 36, "trilialoalkoxy" should read -- trihaloalkoxy --; "trihaloallcylthio" should read -- trihaloalkylthio --; "polyinerizable" should read -- polymerizable --.

Column 15.
Line 12, "ethyhnethacrylate" should read -- ethylmethacrylate --; "2-ethyihexyl should read -- 2-ethylhexyl --;
Line 14, "aniinoplast" should read -- aminoplast --;
Line 62, "ailcylsulfonyl" should read -- alkylsulfonyl --;
Line 63, "polynierizable" should read -- polymerizable --;
Line 65, "maleimick" should read -- maleimide --.

Column 16,
Line 3, "alkylsulfonA" should read -- alkylsulfonyi --;
Lines 4 and 43, "trilialoalkoxy" should read -- trihaloalkoxy --; "trihaloallcylthio" should read -- trihaloalkylthio --; "polyinerizable" should read -- polymerizable --;
Line 34, "ailcylsulfonyl" should read -- alkylsulfonyl --;
Line 35, "polynierizable" should read -- polymerizable --;
Line 37, "maleimick" should read -- maleimide --;

Column 17,
Line 22, "2-ethyihexyl" should read -- 2-ethylhexyl --;
Line 51, "phoiopolymerizable" should read -- photopolymerizable --.

UNITED STATES PATENT AND TRADEMARK OFFICE
CERTIFICATE OF CORRECTION

PATENT NO. : 6,797,841 B2
DATED : September 28, 2004
INVENTOR(S) : Santobianco et al.

It is certified that error appears in the above-identified patent and that said Letters Patent is hereby corrected as shown below:

Column 18,
Line 3, "methylethylamino" should read -- methylethanolamino --;
Line 4, "methylmethylacrylatcamino" should read -- methylmethylacrylateamino --;
Lines 6 and 36, "malcimideamino" should read -- maleimideamino --;
Line 19, "east" should read -- least --;
Line 23, "phoiopolymerizable" should read -- photopolymerizable --;
Line 48, "inteaer" should read -- integer --;
Line 50, "triothanolamine" should read -- triethanolamine --.

Signed and Sealed this

First Day of February, 2005

JON W. DUDAS
*Director of the United States Patent and Trademark Office*